United States Patent [19]

Harris et al.

[11] 4,042,694

[45] * Aug. 16, 1977

[54] NOVEL HETEROCYCLIC ESTERS OF BENZOPYRANOPYRIDINES

[75] Inventors: Louis Selig Harris, Richmond, Va.; Harry George Pars; John Clark Sheehan, both of Lexington, Mass.; Raj Kumar Razdan, Belmont, Mass.

[73] Assignee: Sharps Associates, Cambridge, Mass.

[*] Notice: The portion of the term of this patent subsequent to Nov. 9, 1993, has been disclaimed.

[21] Appl. No.: 664,907

[22] Filed: Mar. 8, 1976

Related U.S. Application Data

[63] Continuation-in-part of Ser. No. 311,953, Dec. 4, 1972, Pat. No. 3,991,194, which is a continuation-in-part of Ser. No. 212,819, Dec. 27, 1971, abandoned.

[51] Int. Cl.$^2$ .................................... C07D 491/04
[52] U.S. Cl. .............................. 424/248.55; 424/267; 260/293.58
[58] Field of Search .......... 260/240 R, 240 D, 240 K, 260/247.2 B, 268 TR, 293.58, 295 T, 243 B; 424/246, 248, 250, 263, 267

[56] References Cited

U.S. PATENT DOCUMENTS

| | | | |
|---|---|---|---|
| 3,452,046 | 6/1969 | Yale et al. | 260/327 |
| 3,509,163 | 4/1970 | Brandstrom et al. | 260/94.7 |
| 3,514,464 | 5/1970 | Pars et al. | 260/295 |
| 3,522,260 | 7/1970 | Shulgin | 260/294.3 |
| 3,542,789 | 11/1970 | Satzinger | 260/293.4 |
| 3,656,906 | 4/1972 | Bullock | 23/230 B |
| 3,728,360 | 4/1973 | Pars et al. | 260/345.3 |
| 3,787,424 | 1/1974 | Pars et al. | 260/295 T |
| 3,991,194 | 11/1976 | Harris et al. | 424/246 |

OTHER PUBLICATIONS

Buzas et al., Compt. Rend. 256, 1804–1806 (1963).

Primary Examiner—John D. Randolph
Attorney, Agent, or Firm—Merriam, Marshall, Shapiro & Klose

[57] ABSTRACT

Novel heterocyclic esters of benzopyranopyridines represented by the formula

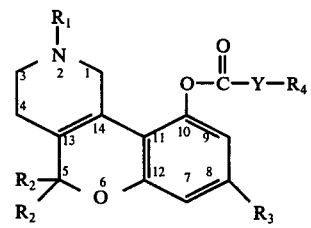

wherein $R_1$ is hydrogen, lower alkyl, lower alkanoyl, cycloalkyl-lower alkyl, cycloalkyl-lower alkanoyl, lower alkenyl, lower alkynyl, halo-loweralkenyl, phenyl-lower alkyl, phenyl-lower alkenyl or phenyl-lower alkynyl; $R_2$ is lower alkyl; $R_3$ is an alkyl having one to twenty carbon atoms or a cycloalkyl-lower alkyl, Y is a straight or branched chain alkylene having one to eight carbon atoms, and $R_4$ is a group of the formula

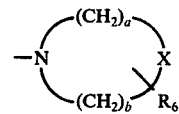

$a$ is an integer from 1 to 4, $b$ is an integer from 1 to 4 and X is $CH_2$, O, S or N—$R_5$ with $R_5$ being hydrogen or lower alkyl, with the limitation that when X is O, S or N—$R_5$, $a$ and $b$ each must be 2 and $R_6$ is hydrogen or a lower alkyl group bonded to a carbon in the ring; and the acid addition salts thereof.

13 Claims, No Drawings

NOVEL HETEROCYCLIC ESTERS OF BENZOPYRANOPYRIDINES

CROSS-REFERENCE TO RELATED APPLICATION

This application is a continuation-in-part of our co-pending patent application Ser. No. 311,953 filed Dec. 4, 1972, now U.S. Pat. No. 3,991,194, which in turn is a continuation-in-part of co-pending patent application Ser. No. 212,819, filed Dec. 27, 1971, now abandoned.

DETAILED DESCRIPTION OF THE INVENTION

This invention relates to novel heterocyclic esters of benzopyranopyridines, to methods of preparing the compounds, to pharmaceutical compositions containing the compounds and to use of the compounds and pharmaceutical compositions containing the compounds for pharmacological and medicinal purposes.

According to one aspect of this invention, compounds are provided which can be represented by the formula

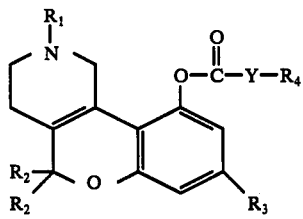

Formula 1 wherein $R_1$ is hydrogen, lower alkyl, lower alkanoyl, cycloalkyl-lower alkyl, cycloalkyl-lower alkanoyl, lower-alkenyl, lower-alkynyl, halo-lower-alkenyl, phenyl-lower alkyl, phenyl-lower alkenyl or phenyl-lower alkynyl; $R_2$ is lower alkyl; $R_3$ is an alkyl having one to twenty carbon atoms or cycloalkyl-lower alkyl, Y is a straight or branched chain alkylene having one to eight carbon atoms, and $R_4$ is a group of the formula

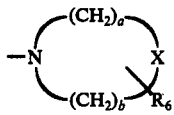

wherein $a$ is an integer from 1 to 4, $b$ is an integer from 1 to 4 and X is $CH_2$, O, S or $N-R_5$, $R_5$ being hydrogen or lower alkyl, with the limitation that when X is O, S, or $N-R_5$, $a$ and $b$ each must be 2 and $R_6$ is hydrogen or a lower alkyl group bonded to a carbon in the ring; and the acid addition salts thereof.

The term "lower alkyl" as used herein, refers to $C_1$-$C_6$ straight or branched chain alkyl groups including methyl, ethyl, n-propyl, iso-propyl, n-butyl, sec-butyl, tert-butyl, n-pentyl, iso-pentyl, neo-pentyl, n-hexyl and the like.

The term "lower alkenyl" refers to straight and branched chain $C_2$-$C_6$ alkyl radicals from which is hydrogen atom has been removed from each of two adjacent carbon atoms to produce ethylenic unsaturation; e.g. vinyl, allyl, methallyl, 1-pentenyl and the like.

The term "lower alkynyl" refers to $C_2$-$C_6$ alkyl groups as defined above, from which two hydrogen atoms have been removed from each of the adjacent carbon atoms to produce acetylenic unsaturation; e.g., ethynyl, propargyl, 2-butynyl, 1-pentynyl and the like groups.

The term "halo" includes chloro, fluoro, bromo and iodo.

The term "lower alkanoyl" refers to saturated, monovalent; aliphatic radicals derived from a monocarboxylic acid, including straight or branched chain radicals of from one to six carbon atoms including the formyl, acetyl, propionyl, α-methylpropionyl, butyryl, hexanoyl and the like radicals.

"Cycloalkyl," as used herein, refers to cyclic, saturated aliphatic radicals having three to eight carbon atoms in a ring, such as cyclopropyl, cyclobutyl, cyclopentyl, cyclohexyl, cycloheptyl and cyclooctyl.

"Cycloalkyl-lower alkyl" refers to groups such as cyclopropyl-methyl, 2-methylcyclobutyl and the like.

The term "alkyl" refers to straight and branched chain alkyl radicals having from one to 20 carbon atoms such as methyl, n-amyl, 3-methyl-2-octyl, 2-nonyl, 2-eicosanyl and the like.

The term "acid addition salts" refers to non-toxic salts prepared by reacting the basic esters of the benzopyranopyridines with an organic or inorganic acid, or by reacting the benzopyranopyridines with the salt of an appropriate acid. Representative salts include the hydrochloride, hydrobromide, sulfate, bisulfate, acetate, valerate, oleate, laurate, borate, benzoate, lactate, phosphate, tosylate, citrate, maleate, succinate, tartrate, napsylate and the like. Such salts are well known in the art and are considered to be "pharmaceutically acceptable."

The compounds provided by the invention considered particularly useful are those of the formula

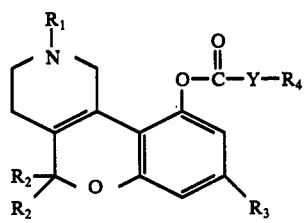

Formula 2 in which $R_1$ is lower alkynyl, each $R_2$ is methyl, $R_3$ is an alkyl group having five to nine carbon atoms, Y is a branched or straight chain alkylene having two to five carbon atoms and, in the groups represented by $R_4$ in Formula 1, $a$ and $b$ are the same or different integers from 1 to 3 and $a + b$ is an integer from 3 to 5, $R_6$ is hydrogen or lower alkyl, and X is $CH_2$ or 0. The preferred compounds are those in which $R_1$ is propargyl, $R_3$ is 3-methyl-2-octyl or pentyl and the sum of $a + b$ is 3 or 4.

Generally speaking, the esters of this invention are prepared by reacting equimolar quantities of the corresponding benzopyranopyridines, and the appropriate acid or its salt, in the presence of a carbodiimide, such as dicyclohexylcarbodiimide, in a suitable solvent such as methylene chloride, chloroform and the like. This reaction can be represented s follows:

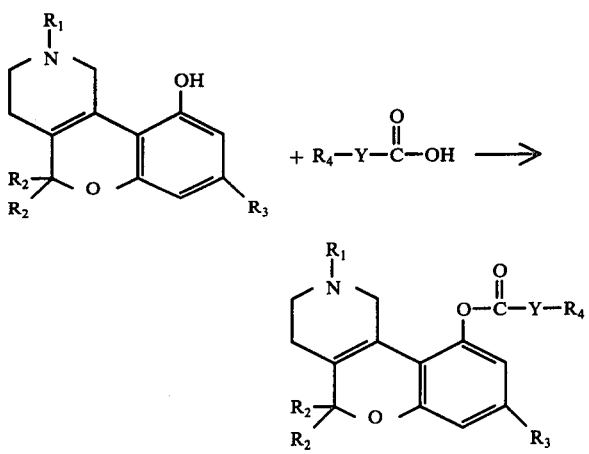

wherein $R_1$, $R_2$, $R_3$, $R_4$ and Y are defined above.

The benzopyranopyridine starting compounds and their preparation are disclosed in U.S. Pat. Nos. 3,576,798 and 3,522,260.

Some of the heterocyclic acids which can be used in the process are:
γ-piperidinobutyric acid,
γ-morpholinobutyric acid,
γ-(2-methylpiperidino)butyric acid,
δ-piperidinovaleric acid,
γ-pyrrolidinobutyric acid,
β-piperidinopropionic acid,
γ-thiomorpholinobutyric acid and
homopiperidinoactic acid.

Reaction between the benzopyranopyridine starting material and the heterocyclic acid, or salt thereof, is readily effected by combining about equimolar amounts of the reactants and a equimolar amount, or slight excess, or a carbodiimide such as dicyclohexylcarbodiimide. The reaction proceeds readily at room temperature and is generally completed in about 4 to 20 hours. After the reaction is terminated, the reaction mixture can be filtered to remove the by-product of dicyclohexylurea, and the solvent can be distilled off using a rotary evaporator. The residue can be directly crystallized from a suitable solvent such as benzene/ether or the residue can be chromatographed and the desired material isolated from the appropriate chromatographic fractions. If the basic esters are obtained, the acid addition salts such as those named above, if desired, can be prepared by methods well known in the art.

The compounds of this invention, in the form of the free bases, can be used as neutralizing agents since they form salts with acids.

The pharmacological activity of the compounds of this invention renders them potentially useful as drugs, both in humans and lower animals, although it should be understood that every compound of the invention will not necessarily have each activity possessed by the others.

The compounds of this invention are useful as analgesic agents, and generally at oral dosages of from 5 to 20 mg./kg. of body weight daily. Lower dosages of the compounds in the range of 0.005 to 5 mg./kg. also induce analgesic activity intravenously and some of the compounds induce this activity at such dosages orally. In test animals, the compounds appear to be in the potency range of α-d-propoxyphene and codeine.

The compounds additionally exhibit mild tranquilizing activity, and generally at oral dosages of from 0.1 to 20 mg./kg. of body weight.

The compounds also exert anticonvulsant activity and sedative-hypnotic activity in animals.

The amount of active ingredient administered may be varied; however, it is necessary that the amount of active ingredient be such that a suitable dosage is given. The selected dosage depends upon the desired therapeutic effect, on the route of administration and on the duration of treatment.

Specific activity for some of the compounds of the invention will now be presented.

The following references may be referred to for details of test procedures used in pharmacologically evaluating the compounds of this invention:

TEST PROCEDURES FOR EVALUATING ANALGESIC ACTIVITY

1. J. Pharmacol. Exper. Therap., 80, 300 (1944) and J. Pharmacol. Exper. Therap., 98, 121 (1950); hot plate test.
2. J. Pharmacol. Exper. Therap., 72, 74 (1941) and J. Pharmacol, Exper. Therap., 169, 17 (1969); rat tail flick test.
3. Brit. J. Pharmacol., 22, 296 (1964); acetic acid induced writhing test.

TEST PROCEDURES FOR EVALUATING TRANQUILIZING ACTIVITY

1. Plotnikoff, U.S. Pat. No. 3,755,586; rat motor activity test and antagonism to methamphetamine-induced hyperirritability.
2. J. Pharmacol. Exper. Therap., 125, 28–34 (1959); suppression of mouse fighting behavior induced by footshock.

MISCELLANEOUS TEST PROCEDURES FOR OTHER ACTIVITIES

1. Experimental Neurology, 15, 463–474 (1966); sedativehynotic test with modifications.
2. J. Pharmacol. Exper. Therap., 119, 294 (1957); anticonvulsant-audiogenic seizure test.

The compound of Example 1 (SP-106) is a tranquilizing agent in mice at 5 to 10 mg./kg. orally; an analgesic agent at 4 to 12 mg./kg. orally in mice and rats; and a sedativehypnotic agent in cats and monkeys at 0.5 to 1.0 mg./kg. orally.

The compound of example 2 (SP-112) is a tranquilizing agent in mice at 5 to 10 mg./kg. orally; an analgesic agent in mice and rats at 9 to 12 mg./kg. orally; and a sedativehynotic agent at 1 mg./kg. orally in cats and monkeys.

The compound of Example 3 (SP-159) is a tranquilizing agent in mice at 5 and 10 mg./kg. orally and it is an anticonvulsant agent in mice at 30 mg./kg. orally. The compound also showed analgesic activity in the writhing and rat tail flick tests. In the sedative-hypnotic test SP-159 is active at 0.5 mg./kg. orally, and produces an increase in total sleep time over control values.

The compound of Example 4 (SP-158) is a tranquilizing agent in mice at 5 and 10 mg./kg. orally and it is an anticonvulsant agent in mice at 30 1 mg./kg. orally.

The compound of Example 5 (SP-167) is a tranquilizing agent in mice at 10 mg./kg. orally and it is an anticonvulsant agent in mice at 30 mg./kg. orally.

The compound of Example 6 (SP-171) is a tranquilizing agne in mice at 5 mg./kg. orally.

The compound of Example 8 (SP-178) has analgesic activity. In the mouse hot plate test it had an $ED_{50}$ of 4.6 mg./kg. orally; in the acetic acid writhing test it had an $ED_{50}$ of 12.2 mg./kg. orally; and, in the rat tail flick test it has an $ED_{50}$ of 9.8 mg./kg. orally. SP-178 also has tranquilizing activity in mice at 10 mg./kg. orally. SP-178 is active as a sedative-hypnotic agent at 0.25 to 2.0 mg./kg. orally.

The compound of Example 20 (SP-204) like SP-106 of Example 1 has potent analgesic activity as demonstrated in three tests. SP-204 exhibited an oral $ED_{50}$ value of 10.7 mg./kg. in the rate tail flick test, thus showing marked activity. SP-204 exhibited an oral $ED_{50}$ value of 7.3 mg./kg. in the acetic acid induced writhing test in mice, thus showing marked activity. In the mouse hot plate test SP-204 had an oral $ED_{50}$ of 3.8 mg./kg. When the compound is administered intravenously in this testing procedure, the $ED_{50}$ value is 1.2 mg./kg. as compared to an $ED_{50}$ value of 4.3 mg./kg. intravenously for morphine.

Unlike SP-106 of Example 1, SP-204 showed little or slight activity in tests which measure potential tranquilizing activity. These testing procedures include the rat motor activity test, the mouse fighting test and the methamphetamine-induced hyperirritability test in rats where SP-204 did not shown any significant antagonism at oral doses of 5 to 40 mg./kg.

Both SP-106 and SP-204 show sedative-hypnotic activity in cats, but a definite difference in potency is not now clearly established. In sedative-hypnotic tests in cats, SP-204 was active at oral doses of 0.5 and 1.0 mg./kg.

In summary, SP-106 (Example 1) has potent analgesic activity and significant tranquilizing activity in animals. SP-204 (Example 20) also has potent analgesic activity, but little or slight tranquilizing activity. Thus, SP-204 has the desirable property of good analgesic activity without tranquilizing activity. SP-204 also has a greater comparative stability to hydrolysis and lessened cardiovascular effects as compared to SP-106.

The compound of Example 21 (SP-202) has tranquilizing activity in animals which indicates potential human use. SP-202 was active in the rat motor activity test at oral doses of 0.5 to 5.0 mg./kg. and in the mouse fighting test at a dose of 10 mg./kg. orally. The compound was also active in antagonizing methamphetamine-induced hyperirritability in rats at oral doses of 10 to 40 mg./kg., thus further demonstrating its tranquilizing activity.

SP-202 displayed some analgesic activity in the acetic acid induced writhing test in mice, producing a 21% inhibition of writhing at an oral dose of 10 mg./kg. In sedative-hypnotic tests in cats, SP-202 was active at an oral dose of 0.5 mg./kg.

The compound of Example 22 (SP-205) has analgesic and tranquilizing activity in animals which indicates potential human use. The analgesic activity of SP-205 was demonstrated in the acetic acid induced writhing test in mice, where SP-205 had an oral $ED_{50}$ of 14.5 mg./kg. In the rat tail flick test, SP-205 caused a 34% increase in reaction time at an oral dose of 20 mg./kg. The tranquilizing activity of SP-205 was shown in the rat motor activity test where the compound was active at oral doses of 1.25 to 40 mg./kg. At oral doses of 10 to 40 mg./kg., SP-205 antagonized the methamphetamine-induced hyperirritability in rats, thus further demonstrating its tranquilizing activity.

The compound of Example 23 (SP-216) also has tranquilizing and analgesic activity in animals which indicates potential human use. The analgesic activity of SP-216 was shown in the acetic acid induced writhing test in mice where SP-215 had an oral $ED_{50}$ value of 12.3 mg./kg. The $ED_{50}$ value for SP-216 in the mouse hot plate test is 22.3 mg./kg. SP-216 was active in the rat motor activity test at 5 mg./kg. orally, and in the mouse fighting test at an oral dose of 10 mg./kg. At 5 mg./kg. orally the compound was active in antagonizing the methamphetamine-induced hyperirritability in rats, thus further demonstrating its tranquilizing activity. SP-216 was also active in the sedative-hypnotic test at an oral dose of 0.5 mg./kg.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used fo direct administration or they may be used to make tablets or to fill gelatin capsules. Suitable lubricants like magnesium stearate, binders such as gelatin, and disintegrating agents like sodium carbonate in combination with critic acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, generally can contain about 5 to 300 mg. of active agent, although some of the compounds appear to have activity which permits them to be used as low as 0.25 to 1 mg. in a unit dosage form. Thus a range of from a low of about 0.25 to 1 mg. and a high of about 300 mg. may be used.

A typical tablet can have the composition:

|  | Mg |
| --- | --- |
| Active agent (1) | 100 |
| Starch U.S.P. | 57 |
| Lactose U.S.P. | 73 |
| Talc. U.S.P. | 9 |
| Stearic acid | 12 |

(1) Any compound from Examples 1 to 23 can be the active agent.

The compounds of this invention exhibit both oral and parenteral activity and accordingly can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art such as water. Besides indert diluents, such preparations can also include adjuvants such as wetting agents, emulsifying and suspending agents and sweetening, flavoring and perfuming agents.

Preparations for parenteral administration include sterile aqueous or non-aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The following examples are presented to further illustrate the invention.

EXAMPLE 1

5,5-Dimethyl-8-(3-methyl-2-octyl)-10-[4-(piperidino)butyryloxy]-2-(2-propynyl)-1,2,3,4-tetrahydro-5H-[1]benzopyrano[3,4-d]pyridine hydrochloride (SP-106)

4.5 g. (11.4 mm.) of 5,5-Dimethyl-10-hydroxy-8-(3-methyl-2-octyl)-2-(2-propynyl)-1,2,3,4-tetrahydro-5H-[1] benzopyrano[3,4-d]pyridine, 2.58 g. (12.5 mm.) of dicyclohexylcarbodiimide and 2.49 g. (12.0 mm.) of γ-piperidinobutyric acid hydrochloride [Cruickshank and Sheehan, J. Am. Chem. Soc., 83, 2891 (1961)], m.p. 190°–192° C., were combined in 250 ml. of methylene chloride and stirred at room temperature for 16 hours. The insoluble by-product of dicyclohexylurea was separated by filtration and the methylene chloride was removed using a rotary evaporator. The residue was dissolved in benzene or benzene/cyclohexane mixtures and filtered several times to remove a small amount of insoluble material. The solvent was evaporated and the residue was dissolved in water and lyophilized to give 2.3 g. (37%) of the product as a light yellow solid.

The material showed an $R_f$ of 0.5 in thin layer chromatography (10% MeOH/CHCl$_3$); the infrared and nuclear magnetic resonance spectra were in agreement with the proposed structure.

Analysis Calcd. for $C_{35}H_{53}ClN_2O_3 \cdot 2\text{-}\frac{1}{2}$ H$_2$O (MW = 630.27): C, 66.70; H, 9.29; N, 4.46. Found: C, 66.58; H, 8.93; N, 4.54.

EXAMPLE 2

5,5-Dimethyl-10-[4-(morpholino)butyryloxy]-8-(3-methyl-2-octyl)-2-(2-propynyl)-1,2,3,4-tetrahydro-5H-[1]benzopyrano[3,4-d] pyridine hydrochloride (SP-112)

0.6 g. (1.51 mm.) of 5,5-Dimethyl-10-hydroxy-8-(3-methyl-2-octyl)-2-(2-propynyl)-1,2,3,4-tetrahydro-5H-[1] benzopyrano[3,4-d]pyridine, 0.317 g. (1.51 mm.) of γ-morpholinobutyric acid hydrochloride [Cruickshank and Sheehan, J. Am. Chem. Soc., 83, 2891 (1961)] and 0.34 g. (1.65 mm.) of dicyclohexylcarbodiimide were combined in 40 ml. of methylene chloride and stirred for 16 hours at room temperature. The insoluble by-product of dicyclohexylurea was removed by filtration and the methylene chloride was distilled off using a rotary evaporator. The residue was dissolved in a small amount of benzene and ether was added to give 0.4 g. of material. Recrystallization from methylene chloride/ligroin (b.p. 100°–115° C) gave 0.3 g. (31%) of product as a beige solid, m.p. 158°–161° C. The sample was found pure by thin layer chromatography (20% MeOH/CHCl$_3$). The infrared and nuclear magnetic resonance spectra were consistent with the proposed structure.

Analysis Calcd. for $C_{34}H_{51}ClN_2O_4 \cdot 2\text{-}\frac{1}{2}$ H$_2$O (MW = 632.26): C, 64.60; H, 8.93; N, 4.43. Found: C, 64.32; H, 8.54; N, 4.31.

EXAMPLE 3

5,5-Dimethyl-10-[4-(2-methylpiperidino)butyryloxy]-8-(3-methyl-2-octyl)-2-(2-propynyl)-1,2,3,4-tetrahydro-5H-[1]benzopyrano [3,4-d]pyridine hydrochloride (SP-159)

14.0 g. (0.07 mole) of methyl γ-(2-methylpiperidino)butyrate was dissolved in 180 ml. of 18% hydrochloric acid solution (90 ml. water and 90 ml. concentrated hydrochloric acid) and refluxed for 16 hours. The excess water was removed using reduced pressure (water aspirator) to give a semi-solid residue which was triturated with acetone and filtered. 11.3 g. (73%) of γ-(2-methylpiperidino)butyric acid hydrochloride was obtained as colorless crystals, m.p. 180°–182° C.

A mixture of 3.0 g. (7.6 mm.) of 5,5-dimethyl-10-hydroxy-8-(3-methyl-2-octyl)-2-(2-propynyl)-1,2,3,4-tetrahydro-5H-[1]benzopyrano[3,4-d] pyridine, 1.68 g. (7.6 mm.) of γ-(2-methylpiperidino)butyric acid hydrochloride and 1.65 g.(8.0 mm.) of dicyclohexylcarbodiimide in 150 ml. of methylene chloride was stirred at room temperature for 16 hours. The reaction mixture was cooled and the solid removed by suction filtration. The methylene chloride was evaporated to give a residue which was dissolved in 8 ml. of methylene chloride and 58 ml. diethyl ether. After standing for 3 days, a total of 100 mg. of solid was removed by gravity filtration. The solvents were evaporated and the gummy resin was dried to give a foam-like residue which was triturated with 30 ml. of diethyl ether. The resulting nearly colorless, gummy residue was dried to give 2.8 g. (61%) of tan solid.

The sample was pure by thin layer chromatography (5% MeOH/CHCl$_3$); the infrared and nuclear magnetic resonance spectra were in agreement with the proposed structure.

Analysis Calcd. for $C_{36}H_{55}ClN_2O_3$ (MW = 599.28): C, 72.14; H, 9.25; N, 4.67. Found: C, 71.94; H, 9.16; N, 4.58.

EXAMPLE 4

5,5-Dimethyl-10-[5-(piperidino)varleryloxy]-8-(3-methyl-2-octyl)-2-(2-propynyl)-1,2,3,4-tetrahydro-5H-[1]benzopyrano[3,4-d] pyridine hydrochloride (SP-158)

A mixture of 25.0 g. (0.167 mole) of methyl δ-chlorovalerate and 37.5 g. (0.25 mole) of sodium iodide in 120 ml. of acetone was stirred and heated at reflux for 16 hours. After cooling the mixture, a solid was removed by suction filtration, and the acetone was distilled off using a rotary evaporator. The residue was dissolved in 300 ml. of diethyl ether, and additional solid was removed by filtration. The ethereal solution was washed twice with a 10% sodium thiosulfate solution, once with water, and dried over sodium sulfate. The ether was evaporated and the residue distilled at b.p. 107°–110° C (15 mm.) to give 30.0 g. (74%) of methyl δ-iodovalerate as a light yellow liquid.

30.0 g. (0.124 mole) of methyl δ-iodovalerate and 42.5 g. (0.50 mole) of piperidine were dissolved in 250 ml. of benzene and heated at 60° C for 3 hours with stirring. A colorless solid began to appear shortly after the materials were combined. The solid was removed by suction filtration, and the benzene evaporated to give methyl δ-piperidinovalerate which distilled at 23.5 g. (95%) of colorless liquid, b.p. 122°–124° C (12.5 mm.).

23.5 g. (0.117 mole) of methyl δ-piperidinovalerate was dissolved in a combination of 125 ml. of concentrated hydrochloric acid and 125 ml. of water and refluxed with stirring for 16 hours. The excess water was removed using reduced pressure (water aspirator) to give a semi-solid residue which was triturated with acetone, filtered and dried. 21.0 g. (79%) of colorless crystals of δ-piperidinovaleric acid hydrochloride was obtained with a m.p. of 202°–204° C.

A mixture of 2.4 g. (6.06 mm.) of 5,5-dimethyl-10-hydroxy-8-(3-methyl-2-octyl)-2-(2-propynyl)-1,2,3,4-tetrahydro-5H-[1]benzopyrano[3,4-d]pyridine, 1.35 g. (6.06 mm.) of δ-piperidinovaleric acid hydrochloride and 1.30 g. (6.30 mm.) of dicyclohexylcarbodiimide in 100 ml. of methylene chloride was stirred at room temperature for 5 hours. The reaction mixture was cooled overnight in the refrigerator and the by-product of dicyclohexylurea removed by suction filtration. The mother liquor was evaporated to give a golden, viscous residue which was dissolved in a mixture of methylene chloride/cyclohexane and allowed to stand in the cold for 2 hours. Gravity filtration separated a small amount of solid which had appeared, and the solvents were removed using a rotary evaporator. Crystallization from methylene chloride/diethyl ether gave 2.5 g. (69%) of colorless crystals, m.p. 140°–144° C. The sample was pure by thin layer chromatography (10% MeOH/CHCl$_3$) and the infrared and nuclear magnetic resonance spectra were in agreement with the proposed structure.

Analysis Calcd. for $C_{36}H_{55}ClN_2O_3$ (MW = 599.28): C, 72.14; H, 9.25; N, 4.67. Found: C, 72.00; H, 9.11; N, 4.63.

EXAMPLE 5

5,5-Dimethyl-10-[4-pyrrolidino)butyryloxy]-8-(3-methyl-2-octyl)-2-(2-propynyl)-1,2,3,4-tetrahydro-5H-[1]benzopyrano [3,4-d]pyridine dihydrochloride (SP-167)

30.0 g. (0.13 mole) of methyl γ-iodobutyrate [Blicke et al, J. Am. Chem. Soc., 63, 2488 (1941)] was combined with 36 g. (0.5 mole) of pyrrolidine in 300 ml. of benzene and heated at 60° C for 0.5 hour and stirred at room temperature for 16 hours. A dark orange layer formed, and the benzene solution was decanted, concentrated and distilled to give 10 g. of colorless liquid. This material was dissolved in a combination of 50 ml. of concentrated hydrochloric acid and 50 ml. of water and heated at reflux for 28 hours. The solution was concentrated under reduced pressure to give a semi-solid residue which was triturated with acetone and filtered. Recrystallization from a combination of 11 ml. of acetic acid/40 ml. of acetone gave 8.3 g. (33%) of colorless crystals of γ-pyrrolidinobutyric acid hydrochloride, m.p. 126–127° C.

3.0 g. (7.57 mm.) of 5,5-dimethyl-10-hydroxy-8-(3-methyl-2-octyl)-2-(2-propynyl)-1,2,3,4-tetrahydro-5H-[1]benzopyrano[3,4-d]pyridine was combined with 1.45 g. (7.57 mm.) of γ-pyrrolidinobutyric acid hydrochloride and 1.67 g. (8.12 mm.) of dicyclohexylcarbodiimide in 150 ml. of methylene chloride and stirred at room temperature for 3 hours. The reaction mixture was stored for 16 hours in the cold, and the by-product of dicyclohexylurea was removed by suction filtration. After evaporation of the solvent, the resulting gummy residue was dissolved in a mixture of 25 ml. of methylene chloride and 65 ml. of cyclohexane and allowed to stand at room temperature for 2 hours and at 5° C for 16 hours. A small quantity of solid was separated by gravity filtration, and the solvents were removed on a rotary evaporator. Crystallization from methylene chloride and diethyl ether gave 0.75 g. (16%) of the desired product as the dihydrochloride, a colorless solid having a melting point of 168°–171° C which was pure by thin layer chromatography (10% MeOH/CHCl$_3$). The infrared and nuclear magnetic resonance spectra were in agreement with the proposed structure.

Analysis Calcd. for $C_{34}H_{52}Cl_2N_2O_3 \cdot H_2O$ (MW = 624.70): C, 65.35; H, 8.54; N, 4.48. Found: C, 65.24; H, 8.32; N, 4.58.

EXAMPLE 6

5,5-Dimethyl-10-[4-(piperidino)butyryloxy]-2-(2-propynyl)-8-pentyl-1,2,3,4-tetrahydro-5H-[1]benzopyrano[3,4-d]pyridine hydrochloride (SP-171)

A mixture of 1.45 g. (4.26 mm.) of 5,5-dimethyl-10-hydroxy-2-(2-propynyl)-8-pentyl-1,2,3,4-tetrahydro-5H-[1]benzopyrano[3,4-d]pyridine, 0.89 g. (4.28 mm.) of γ-piperidinobutyric acid hydrochloride and 0.93 g. (4.50 mm.) of dicyclohexylcarbodiimide in 200 ml. of methylene chloride was stirred at room temperature for 18 hours. After cooling the reaction mixture for 1-½ hours, the by-product of dicyclohexylurea was removed by suction filtration. A rotary evaporator was used to remove the methylene chloride, and a mixture of 25 ml. of methylene chloride and 50 ml. of cyclohexane was added. After standing at room temperature for 2 hours and at 5° C for 16 hours, gravity filtration was used to separate 300 mg. of solid. This material proved to be a mixture of the starting acid hydrochloride and the hydrochloride salt of the starting benzopyran. The mother liquor was evaporated and the residue was crystallized from a mixture of 2 ml. of methylene chloride and 15 ml. of diethyl ether. After filtration and drying, a total of 0.5 g. (22%) of colorless solid was obtained. The sample was pure by thin layer chromatography (10% MeOH/CHCl$_3$). The infrared and nuclear magnetic resonance spectra were in agreement with the proposed structure.

Analysis Calcd. for $C_{31}H_{45}ClN_2O_3 \cdot \frac{1}{2}H_2O$ (MW = 538.15): C, 69.18; H, 8.61; N, 5.20. Found: C, 69.08; H, 8.74; N, 5.20.

EXAMPLE 7

5,5-Dimethyl-8-(3-methyl-2-octyl)-10-[4-(piperidino)butyryloxy]-2-(2-propynyl)-1,2,3,4-tetrahydro-5H-[1]benzopyrano[3,4-d]pyridine hydrochloride (SP-106)

The preparation of this compound was repeated by combining equimolar quantities of 5,5-dimethyl-10-hydroxy-8-(3-methyl-2-octyl)-2-(2-propynyl)-1,2,3,4-tetrahydro-5H-[1]benzopyrano[3,4-d]pyridine, dicyclohexylcarbodiimide and γ-piperidinobutyric acid hydrochloride in methylene chloride. After stirring for about 16 hours at room temperature, the reaction mixture was cooled, and the by-product of dicyclohexylurea was removed by suction filtration. The mother liquor was evaporated to give a light yellow residue which was dissolved in a methylene chloride/cyclohexane mixture and stored in the cold for 16 hours. A small quantity of additional dicyclohexylurea was removed by filtration, and the solvents were distilled off using a rotary evaporator. The residue which remained was dried in vacuo and crystallized from a mixture of methylene chloride and diethyl ether to give a colorless solid, m.p. 108°–111° C. Thin layer chromatography (10% MeOH/CHCl$_3$) indicated the compound to be pure; the nuclear magnetic resonance and infrared spectra of the material were consistent with the desired product.

Analysis Calcd. for $C_{35}H_{53}ClN_2O_3$ (MW = 585.24): C, 71.80; H, 9.12; N, 4.78. Found: C, 71.82; H, 9.17; N, 4.85.

A second crop of material was obtained by work-up of the mother liquor, and this material appeared similar to the main batch in all ways.

Analysis: Found: C, 71.66; H, 9.05; N, 4.76 Total yield for both batches was 95%.

EXAMPLE 8

5,5-Dimethyl-10-[2-methyl-4-(piperidino)butyryloxy]-8-(3-methyl-2-octyl)-2-(2-propynyl)-1,2,3,4-tetrahydro-5H-[1]benzopyrano[3,4-d]pyridine dihydrochloride (SP-178)

The method of Lee V. Phillips (U.S. Pat. No. 3,299,100) was used to prepare α-methyl-γ-butyrolactone and this material was converted to ethyl γ-bromo-α-methylbutyrate via the procedure of G. Jones and J. Wood, "The Synthesis of 9-Azasteroids-II", Tetrahedron, 21, 2961 (1965).

10.5 g. (0.05 mole) of ethyl γ-bromo-α-methylbutyrate was combined with 17.0 g. (0.20 mole) of piperidine and 100 ml. of benzene and stirred for 16 hours at room temperature and heated at 60° C for 4 hours. The reaction mixture was cooled and the colorless solid which appeared was removed by filtration. The mother liquor was concentrated to give ethyl α-methyl-γ-piperidinobutyrate as a mobile yellow liquid which distilled (b.p. 78° C at 0.25 mm.) as 6.7 g. (63%) of colorless liquid. The nuclear magnetic resonance and infrared spectra were consistent with the desired compound.

6.5 g. (0.030 mole) of ethyl α-methyl-γ-piperidinobutyrate was combined with a mixture of 45 ml. of water and 45 ml. of concentrated hydrochloric acid and heated at reflux for 16 hours. The solution was concentrated under reduced pressure (water aspirator) to give a residue which crystallized upon addition of 50 ml. of diethyl ether. The ether was decanted, and the solid was triturated with acetone and filtered. Recrystallization from acetic acid/acetone gave 3.38 g. of α-methyl-γ-piperidinobutyric acid hydrochloride as colorless crystals, m.p. 166°-168° C and a second crop of 1.27 g. of solid, m.p. 165°-168° C. The total yield for both batches was 69%. The nuclear magnetic resonance and infrared spectra were in agreement with the proposed structure.

2.0 g. (5.05 mm.) of 5,5-dimethyl-10-hydroxy-8-(3-methyl-2-octyl)-2-(2-propynyl)-1,2,3,4-tetrahydro-5H-[1]benzopyrano[3,4-d]pyridine was combined with 1.12 g. (5.05 mm.) of α-methyl-γ-piperidinobutyric acid hydrochloride and 1.08 g. (5.25 mm.) of dicyclohexylcarbodiimide in 110 ml. of methylene chloride and the mixture was stirred at room temperature for 16 hours. After cooling for 4 hours, the by-product of dicyclohexylurea was removed by suction filtration. The motor liquid was evaporated to give a colorless foamy residue which was dissolved in a methylene chloride/cyclohexane mixture and stored for 16 hours in the cold. A small amount of solid was separated by gravity filtration, and the solvents were removed using a rotary evaporator. The residue was dried to give 2.6 g. of colorless solid which was combined with 0.6 g. of material obtained from an earlier preparation. Both samples were dissolved in a mixture of methylene chloride/diethyl ether and converted to the dihydrochloride by the addition of a solution of hydrogen chloride in diethyl ether. The solvents were decanted, and the gummy residue crystallized upon trituration with diethyl ether. The solid was filtered and recrystallized from 20 ml. of methylene chloride/20ml. diethyl ether to give 1.7 g. of 5,5-dimethyl-10-[2-methyl-4-(piperidino)butyryloxy]-8-(3-methyl-2-octyl)-2-(2-propynyl)-1,2,3,4-tetrahydro-5H-[1]benzopyrano[3,4-d]pyridine dihydrochloride as colorless crystals, m.p. 175°-180° C. The nuclear magnetic resonance and infrared spectra were consistent with the desired structure, and the material was pure by thin layer chromatography (10% MeOH/CHCl₃).

Analysis Calcd. for $C_{36}H_{56}Cl_2N_2O_3$ (MW = 635.74): C, 68.00; H, 8.88; N, 4.41. Found: C, 67.96; H, 8.70; N, 4.34.

EXAMPLE 9

5,5-Dimethyl-10-[4-(morpholino)butyryloxy]-8-(3-methyl-2-octyl)-2-(2-propynyl)-1,2,3,4-tetrahydro-5H-[1]benzopyrano[3,4-d]pyridine dihydrochloride (SP-112)

4.0 g. (10.1 mm.) of 5,5-dimethyl-10-hydroxy-8-(3-methyl-2-octyl)-2-(2-propynyl)-1,2,3,4-tetrahydro-5H-[1]benzopyrano[3,4-d]pyridine, 2.10 g. (10.1 mm.) of γ-morpholinobutyric acid hydrochloride and 2.18 g. (10.6 mm.) of dicyclohexylcarbodiimide were added to 200 ml. of methylene chloride. The reaction mixture was stirred at room temperature for 16 hours and after cooling the by-product of dicyclohexylurea was removed by suction filtration. The mother liquor was evaporated to give a residue which after the usual work-up was converted to a dihydrochloride by the addition of an ether solution of hydrogen chloride. Recrystallization from methylene chloride/diethyl ether gave a total of 3.23 g. (52%), m.p. 154°-160° C. The nuclear magnetic resonance and infrared spectra were in agreement with the proposed structure; the material was pure by thin layer chromatography (10% MeOH/CHCl₃).

Analysis Calcd. for $C_{34}H_{52}Cl_2N_2O_4$ (MW = 623.68): C, 65.47; H, 8.40; N, 4.49. Found: C, 65.21; H, 8.45; N, 4.47.

EXAMPLE 10

5,5-Dimethyl-10-[3-(piperidino)propionyloxy]-8-pentyl-2-(2-propynyl)-1,2,3,4-tetrahydro-5H-[1]benzopyrano[3,4-d]pyridine tartrate 5,5-Dimethyl-10-hydroxy-8-pentyl-2-(2-propynyl)-1,2,3,4-tetrahydro-5H-[1]benzopyrano[3,4-d]pyridine (1 mm.), dicyclohexylcarbodiimide (1 mm.) and β-piperidinopropionic acid (1 mm.) are combined in 30 ml. of methylene chloride and stirred for 16 hours. The insoluble by-product of dicyclohexylurea is removed by filtration and the methylene chloride is distilled off using a rotary evaporator. The residue is dissolved in benzene and filtered to remove any insoluble material. The solvent is evaporated and the residue is chromatographed to yield the desired product as neutral material which can be converted to the tartrate by well known methods.

The following compounds are prepared according to the method of Example 10 by reacting the desired benzopyranopyridine with the appropriate acid or acid salt.

EXAMPLE 11

5,5-Dimethyl-8-(3-methyl-2-octyl)-2-(2-propynyl)-1,2,3,4-tetrahydro-10-[4-(thiomorpholino)butyryloxy]-5H-[1]benzopyrano[3,4-d]pyridine hydrobromide Equimolar amounts of 5,5-dimethyl-10-hydroxy-8-(3-methyl-2-octyl)-2-(2-propynyl)-1,2,3,4-tetrahydro-5H-[1]benzopyrano[3,4-d]pyridine, γ-thiomorpholinobutyric acid hydrobromide and dicyclohexylcarbodiimide are reacted to form the desired product.

EXAMPLE 12

5,5-Dimethyl-2-benzyl-10-[2-(homopiperidino)acetoxy]-8-hexyl-1,2,3,4-tetrahydro-5H-[1]benzopyrano[3,4-d]pyridine Equimolar amounts of 5,5-dimethyl-2-benzyl-8-hexyl10-hydroxy-1,2,3,4-tetrahydro-5H-[1]benzopyrano[3,4-d]pryidine, homopiperidinoacetic acid and dicyclohexylcarbodiimide are reacted to form the desired product.

EXAMPLE 13

5,5-Dimethyl-10-[4-(morpholino)butyryloxy]-8-(3-methyl-2-octyl)-2-methyl-1,2,3,4-tetrahydro-5H-[1]benzopyrano 5H-[3,4-d] pyridine hydrochloride 5,5-Dimethyl-10-hydroxy-8-(3-methyl-2-octyl)-2-methyl-1,2,3,4-tetrahydro-5H-[1]benzopyrano[3,4-d]pyridine, γ-morpholinobutyric acid hydrochloride and dicyclohexylcarbodiimide are combined in equimolar amounts in methylene chloride and reacted as in Example 1 to give the desired product.

EXAMPLE 14

2-Benzyl-5,5-dimethyl-10-[4-(morpholino)butyryloxy]-8-(3-methyl-2-octyl)-1,2,3,4-tetrahydro-5H-[1]benzopyrano[3,4-d]pyridine hydrochloride 2-Benzyl-5,5-dimethyl-10-hydroxy-8-(3-methyl-2-octyl)-1,2,3,4-tetrahydro-5H-[1]benzopyrano[3,4-d]pyridine, γ-morpholinobutyric acid hydrochloride and dicyclohexyl-carbodiimide are combined in equimolar amounts in methylene chloride and reacted as in Example 1 to give the desired product.

EXAMPLE 15

2-Benzyl-5,5-dimethyl-10-[4-(2-methylpiperidino)-butyryloxy]-8-(1-pentyl)-1,2,3,4-tetrahydro-5H-[1]benzopyrano[3,4-d]pyridine hydrochloride 2-Benzyl-5,5-dimethyl-10-hydroxy-8-(1-pentyl)-1,2,3,4-tetrahydro-5H-[1]benzopyrano[3,4-d]pyridine, γ-(2-methylpiperidino)butyric acid hydrochloride and dicyclohexylcarbodiimide in equimolar amounts are reacted as in Example 1 to give the desired product.

EXAMPLE 16

5,5-Dimethyl-10-[4-(pyrrolidino)butyryloxy]-2-phenethyl-8-(2-tetradecyl)-1,2,3,4-tetrahydro-5H-[1]benzopyrano[3,4-d]pyridine hydrochloride 5,5-Dimethyl-10-hydroxy-2-phenethyl-8-(2-tetradecyl)1,2,3,4-tetrahydro-5H-[1]benzopyrano[3,4-d]pyridine, γ-pyrrolidinobutyric acid hydrochloride and dicyclohexylcarbodiimide are reacted in equimolar amounts according to Example 1 to form the desired product.

EXAMPLE 17

2-Allyl-5,5-diethyl-8-(3-methyl-2-octyl)-10-[4-(piperidino) butryloxy]-1,2,3,4-tetrahydro-5H-[1]benzopyrano[3,4-d]pyridine hydrochloride 2-Allyl-5,5-diethyl-8-(3-methyl-2-octyl)-10-hydroxy1,2,3,4-tetrahydro-5H-[1]benzopyrano[3,4-d]pyridine, γ-piperidinobutyric acid hydrochloride and dicyclohexylcarbodiimide are reacted in equimolar amounts to produce the desired product.

EXAMPLE 18

2-(2-Cyclohexylethyl)-5,5-dimethyl-8-(1-pentyl)-10-[5-(morpholino)valeryloxy]-1,2,3,4-tetrahydro-5H-[1]benzopyrano [3,4-d]pyridine hydrochloride 2-(2-Cyclohexylethyl)-5,5-dimethyl-10-hydroxy-8-(1-pentyl)-1,2,3,4-tetrahydro-5H-[1]benzopyrano[3,4-d] pyridine, δ-piperidinovaleric acid hydrochloride and dicyclohexylcarbodiimide are reacted in equimolar amounts according to Example 1 to form the desired product.

EXAMPLE 19

2-Cinnamyl-8-cyclopropylmethyl-5,5-di(1-propyl)-10-[4-(pyrrolidino)butyryloxy]-1,2,3,4-tetrahydro-5H-[1]benzopyrano[3,4-d]pyridine hydrochloride 2-Cinnamyl-8-cyclopropylmethyl-5,5-di(1-propyl)10-hydroxy-1,2,3,4-tetrahydro-5H-[1]benzopyrano[3,4-pyridine, γ-pyrrolidinobutyric acid hydrochloride and dicyclohexyl-carbodiimide are reacted in equimolar amounts according to Example 1 to form the desired product.

EXAMPLE 20

5,5-Dimethyl-10-[2-methyl-4-(2-methylpiperidino)-butyryloxy]-8-(3-methyl-2-octyl)-2-2-(2-propynyl)-1,2,3,4-tetrahydro-5H-[1]benzopyrano[3,4-d]pyridine dihydrochloride (SP-204)

A mixture of 32.7 g. (0.155 mole) of ethyl γ-bromo-α-methylbutyrate, 15.3 g. (0.155 mole) of 2-methylpiperidine and 16.5 g. (0.155 mole) of anhydrous sodium carbonate in 500 ml. of methanol was stirred and heated at reflux for 48 hours and stirred at room temperature for 18 hours. The solid was removed by filtration and washed with methanol, and the methanol solution and washings were evaporated. The orange mobile liquid was distilled and three fractions were collected. The first two fractions were discarded and the third fraction was again distilled and refractionated to give 15.60 g. (50%) of colorless liquid, b.p. 68°-72° C (0.2 mm.). The material was pure by gas liquid chromatography (2% methyl phenyl silicone column), and the infrared and nuclear magnetic resonance spectra were in agreement with the proposed structure. From the nuclear magnetic resonance spectrum it was determined that the product transesterified to the methyl ester.

A combination of 15.3 g. (0.073 mole) of methyl α-methyl-γ-(2-methylpiperidino)butyrate, 125 ml. of concentrated hydrochloric acid and 125 ml. of water was refluxed with stirring for 20 hours. The reaction mixture was evaporated under reduced pressure to give an orange-colored viscous residue. The material was combined with 200 ml. of xylene and heated under reflux using a water collector. The xylene was evaporated, and the residue crystallized upon trituration with acetone. The solid was filtered, washed with acetone and diethyl ether and dried to give 14 g. of light beige crystals. A portion of this material was recrystallized from acetone to give 5.0 g. of α-methyl-γ-(2-methylpiperidino)butyric acid hydrochloride as colorless crystals, m.p. 126°–127° C. The nuclear magnetic resonance spectrum of this compound was consistent with the desired product.

Analysis Calcd. for $C_{11}H_{22}ClNO_2$ (MW = 235.7):C, 56.04; H, 9.41; N, 5.94. Found: C, 56.09; H, 9.30; N, 6.00.

A mixture of 4.0 g. (10.1 mmole) of 5,5-dimethyl-10-hydroxy-8-(3-methyl-2-octyl)-2-(2-propynyl)-1,2,3,4-tetrahydro-5H-[1]benzopyrano[3,4-d]pyridine, 2.38 g. (10.1 mmole) of α-methyl-γ-(2-methylpiperidino)butyric acid hydrochloride, and 2.22 g. (10.8 mmole) of dicyclohexylcarbodiimide in 200 ml. of methylene chloride was stirred at room temperature for 5.5 hours. After cooling, the by-product of dicyclohexylurea was removed by suction filtration. The solvent was evaporated and after dissolving the residue in a methylene chloride/diethyl ether mixture, a small amount of insoluble material was again removed by filtration. The ester was converted to the dihydrochloride salt by the addition of ethereal hydrogen chloride. After removal of the solvents and trituration was ether, the solid was filtered and dried to give 6.8 g. of light yellow powder. Crystallization from 30 ml. methylene chloride/50 ml. diethyl ether gave 4.07 g. (62%) of 5,5-dimethyl-10-[2-methyl-4-(2-methylpiperidino)butyryloxy]-8-(3-methyl-2-octyl)-2-(2-propynyl)-1,2,3,4-tetrahydro-5H-[1]benzopyrano-[3,4-d]pyridine dihydrochloride (SP-204) as colorless crystals, m.p. 190°–194° C. The sample was shown to be free of starting material by thin layer chromatography (10% MeOH/CHCl₃), and the infrared and nuclear magnetic resonance spectra were consistent with the desired product. Analysis Calcd. for $C_{37}H_{58}Cl_2N_2O_3$ (MW = 649.74): C, 68.39; H, 8.99; N, 4.31. Found: C, 68.17; H, 8.96; N, 4.40.

EXAMPLE 21

5,5-Dimethyl-10-[2-methyl-4-(morpholino)butyryloxy]-8-(3-methyl-2-octyl)-2-(2-propynyl)-1,2,3,4-tetrahydro-5H-[1]benzopyrano[3,4-d]pyridine dihydrochloride (SP-202)

A mixture of 40.0 g. (0.19 mole) of ethyl γ-bromo-α-methylbutyrate, 66.0 g. (0.76 mole) of morpholine and 750 ml. of benzene was heated at 60°–70° C for a total of 5 hours and stirred at room temperature for 48 hours. The precipitated amine hydrobromide was removed by filtration, and the mother liquor was evaporated and again filtered to remove some additional solid. The material was distilled and fractions collected to give a total of 38 g. (93%) of colorless liquid, b.p. 71°–73° C (0.10 mm.). The material was pure by gas liquid chromatography, and the infrared and nuclear magnetic resonance spectra were in agreement with the proposed structure.

32.0 g. (0.15 mole) of ethyl α-methyl-γ-morpholinobutyrate was combined with a mixture of 200 ml. of concentrated hydrochloric acid and 200 ml. of water and heated at reflux with stirring for 20 hours. The reaction mixture was evaporated under reduced pressure (water aspirator) to give a colorless viscous residue which was crystallized by trituration with acetone. After the solid was filtered, washed with diethyl ether and dried, there was obtained 30.6 g. (92%) of α-methyl-γ-morpholinobutyric acid hydrochloride as colorless crystals, m.p. 155°–157° C. The nuclear magnetic resonance spectrum of this material was in agreement with the proposed structure.

Analysis Calcd. for $C_9H_{18}ClNO_3$ (MW = 223.69): C, 48.32; H, 8.11; N, 6.25. Found: C, 48.29; H, 8.01; N, 6.28.

A combination of 5.0 g. (12.6 mmole) of 5,5-dimethyl-10-hydroxy-8-(3-methyl-2-octyl)-2-(2-propynyl)1,2,3,4-tetrahydro-5H-[1]benzopyrano[3,4-d]pyridine, 2.82 g. (12.6 mmole) of α-methyl-γ-morpholinobutyric acid hydrochloride, 2.78 g. (13.5 mmole) of dicyclohexylcarbodiimide and 250 ml. of methylene chloride was stirred at room temperature for 16 hours. The reaction mixture was cooled and the by-product of dicyclohexylurea was removed by suction filtration. The solvent was removed and the residue dissolved in a mixture of methylene chloride/cyclohexane and again filtered to remove a small amount of insoluble material. After evaporation of the solvents, the material was dissolved in methylene chloride was converted to the dihydrochloride salt by the addition of ethereal hydrogen chloride. The solvents were removed and the residue was recrystallized from a methylene chloride/diethyl ether mixture to give 4.2 g. (52%) of colorless crystals, m.p. 188°–192° C. The sample was shown to be free of starting material by thin layer chromatography (10% MeOH/CHCl₃), and the infrared and nuclear magnetic resonance spectra were consistent with the proposed structure.

Analysis Calcd. for $C_{35}H_{54}Cl_2N_2O_4$ (MW = 637.71): C, 65.91; H, 8.54; N, 4.39. Found: C, 65.83; H, 8.50; N, 4.38.

EXAMPLE 22

5,5-Dimethyl-10-[2,2-dimethyl-4-(piperidino)butyryloxy]-8-(3-methyl-2-octyl)-2-(2-propynyl)-1,2,3,4-tetrahydro-5H-[1]benzopyrano[3,4-d]pyridine dihydrochloride (SP-205)

To a cooled (0°–10° C) solution of 16.5 g. (0.145 mole) of α,α-dimethyl-γ-butyrolactone in 70 ml. of anhydrous ethanol was added anhydrous gaseous hydrogen bromide. Care was taken to keep the temperature at 0°–10° C, and the addition was continued for 2.5 hours. After standing at room temperature for 24 hours, the reaction mixture was again cooled and hydrogen bromide was bubbled in for an additional hour. After 48 hours at room temperature, the reaction mixture was added to 80 g. of ice. The aqueous layer was separated and extracted three times with diethyl ether, and the organic layers were combined, washed twice with 5% sodium bicarbonate solution and water. The solution was dried over sodium sulfate, evaporated, and distilled to give 25.2 g. (78%) of ethyl α,α-dimethyl-γ-bromobutyrate as a colorless liquid, b.p. 83°–85° C (10 mm.). The sample was 95% pure by gas liquid chromatography, and the nuclear magnetic resonance spectrum was in agreement with the desired product.

A mixture of 10.0 g. (0.045 mole) of ethyl α,α-dimethyl-γ-bromobutyrate, 15.3 g. (0.18 mole) of piperidine and 125 ml. of benzene was heated at 60°–70° C for a total of 4 hours and allowed to stand at room temperature for 3 days. The reaction mixture was cooled and filtered to remove the amine hydrobromide which had precipitated. The mother liquor was concentrated, distilled and four fractions were collected. The first three fractions were shown by gas liquid chromatography to contain various quantities of the unreacted bromo compound. Fraction 4 (3.60 g.) was pure by gas liquid chromatography, and the nuclear magnetic resonance spectrum was consistent with the desired ethyl α,α-dimethyl-γ-piperidinobutyrate.

3.3 g. (14.5 mmole) of ethyl α,α-dimethyl-γ-piperidinobutyrate was combined with 25 ml. of concentrated hydrochloric acid and 25 ml. of water and stirred at reflux for 18 hours. The reaction mixture was evaporated under reduced pressure to give a semi-solid residue which crystallized upon trituration with 30 ml. of acetone. The solid was filtered, washed with diethyl ether, and dried to give 2.25 g. (66%) of α,α-dimethyl-γ-piperidinobutyric acid hydrochloride as colorless crystals, m.p. 232°–234° C. The nuclear magnetic resonance spectrum was consistent with the proposed structure.

Analysis Calcd. for $C_{11}H_{22}ClNO_3$ (MW = 235.75): C, 56.00; H. 9.36; N, 5.96. Found: C, 56.04; H, 9.41; N, 5.94.

A mixture of 2.5 g. (6.3 mmole) of 5,5-dimethyl-10-hydroxy-8-(3-methyl-2-octyl)-2-(2-propynyl)-1,2,3,4-tetrahydro-5H-[1]benzopyrano[3,4-d]pyridine, 1.49 g. (6.3 mmole) of α,α-dimethyl-γ-piperidinobutyric acid hydrochloride, 1.39 g. (6.75 mmole) of dicyclohexylcarbodiimide and 125 ml. of methylene chloride was stirred at room temperature for 16 hours. The reaction mixture was cooled and the by-product of dicyclohexylurea was removed by suction filtration. The mother liquor was evaporated to give a residue which was dissolved in a mixture of methylene chloride/diethyl ether and re-filtered to remove a small amount of insoluble material. The solvents were evaporated and the ester converted to a dihydrochloride salt by the addition of ethereal hydrogen chloride to a methylene chloride solution of the compound. The solvents were removed and the dihydrochloride salt was crystallized from a methylene chloride/diethyl ether mixture to give 2.86 g. (70%) of 5,5-dimethyl-10-[2,2-dimethyl-4-(piperidino)butyryloxy]-8-(3-methyl-2-octyl)-2-(2-propynyl)-1,2,3,4-tetrahydro-5H-[1]benzopyrano [3,4-d]pyridine dihydrochloride as colorless crystals, m.p. 143°–150° C. The material was shown to be free of starting material by thin layer chromatography (10% MeOH/CHCl₃), and the infrared and nuclear magnetic resonance spectra were in agreement with the proposed structure.

Analysis Calcd. for $C_{37}H_{58}Cl_2N_2O_3$ (MW = 649.76): C, 68.39; H, 9.00; N, 4.31. Found: C, 68.17; H, 8.71; N, 4.26.

EXAMPLE 23

5,5-Dimethyl-10-[3-(piperidino)propionyloxy]-8-(3-methyl-2-octyl)-2-(2-propynyl)-1,2,3,4-tetrahydro-5H-[1]benzopyrano [3,4-d]pyridine dihydrochloride (SP-216)

A mixture of 2.0 g. (5.05 mmole) of 5,5-dimethyl-10-hydroxy-8-(3-methyl-2-octyl)-2-(2-propynyl)-1,2,3,4-tetrahydro-5H-[1]benzopyrano[3,4-d]pyridine, 0.75 ml. (5.30 mmole) of triethylamine, 0.42 ml. (5.30 mmole) of acryloyl chloride and 25 ml. of methylene chloride was stirred at room temperature for 18 hours. The reaction mixture was evaporated and 50 ml. of diethyl ether was added to the brown semi-solid residue which was obtained. The insoluble solid was removed by filtration, and the mother liquor was removed on a rotary evaporator. The residue which remained was subsequently dissolved in 50 ml. of methylene chloride. After washing twice with 1N hydrochloric acid, twice with 5% sodium bicarbonate solution, twice with water, and drying over sodium sulfate, the methylene chloride was evaporated to give 1.86 g. (82%) of 10-acryloyloxy-5,5-dimethyl-8-(3-methyl-2-octyl)-2-(2-propynyl)-1,2,3,4-tetrahydro-5H-[1]benzopyrano [3,4-d]pyridine as a brown gum. The material showed a single spot by thin layer chromatography (5% MeOH/CHCl₃), and the infrared and nuclear magnetic resonance spectra were consistent with the desired product.

Analysis Calcd. for $C_{29}H_{39}NO_3$ (MW = 449.60): C, 77.46; H, 8.74; N, 3.11. Found: C, 77.24; H, 8.79; N, 3.00.

To a solution of 2.35 g. (5.24 mmole) of 10-acryloyloxy-5,5-dimethyl-8-(3-methyl-2-octyl)-2-(2-propynyl)-1,2,3,4-tetrahydro-5H-[1]benzopyrano[3,4-d]pyridine dissolved in 50 ml. of methylene chloride was added dropwise and with stirring a solution of 0.45 g. (5.24 mmole) of piperidine dissolved in 15 ml. of methylene chloride. After stirring at room temperature for 18 hours, the solvent was removed on a rotary evaporator. The residue was dissolved in 50 ml. of petroleum ether (30°–60° C), and the solution was filtered to remove a small amount of insoluble material. The solvent was evaporated and the ester converted to the dihydrochloride salt by the addition of ethereal hydrogen chloride to a diethyl ether solution (15 ml.) of the compound. An additional 20 ml. of diethyl ether was added, and the ester dihydrochloride was filtered, washed and dried to give 2.55 g. of 5,5-dimethyl-10-[3-(piperidino)propionyloxy]-8-(3-methyl-2-octyl)-2-propynyl)-1,2,3,4-tetrahydro-5H-[1]benzopyrano[3,4-d]pyridine dihydrochloride (SP-216) as colorless crystals. After recrystallization from methylene chloride there was obtained 2.14 g. (67%) of colorless crystals, m.p. 196°–201° C. The sample was pure by thin layer chromatography (10% MeOH/CHCl₃), and the infrared and nuclear magnetic resonance spectra were consistent with the proposed structure.

Analysis Calcd. for $C_{34}H_{52}Cl_2N_2O_3$ (MW = 607.67): C, 67.19; H, 8.63; N, 4.61. Found: C, 66.96; H, 8.77; N, 4.56.

The foregoing detailed description has been given for clearness of understanding only, and no unnecessary limitations should be understood therefrom, as modifications will be obvious to those skilled in the art.

What is claimed is:

1. A compound named 5,5-dimethyl-10-[2-methyl-4-(2-methylpiperidino) butyryloxy]-8-(3-methyl-2-octyl)-2-(2-propynyl)-1,2,3,4-tetrahydro-5H-[1]benzopyrano[3,4-d]pyridine or a pharmaceutically acceptable acid addition salt thereof.

2. The compound of claim 1 as the dihydrochloride salt.

3. A compound named 5,5-dimethyl-10-[2-methyl-4-(morpholino)butyryloxy]-8-(3-methyl-2-octyl)-2-(2-propynyl)-1,2,3,4-tetrahydro-5H-[1]benzopyrano [3,4-d]pyridine or a pharmaceutically acceptable acid addition salt thereof.

4. A compound named 5,5-dimethyl-10-[2,2-dimethyl-4-(piperidino)butyryloxy]-8-(3-methyl-2-octyl)-2-(2-propynyl)-1,2,3,4-tetrahydro-5H-[1]benzopyrano[3,4-d]pyridine or a pharmaceutically acceptable acid addition salt thereof.

5. A compound named 5,5-dimethyl-10-[3-(piperidino)propionyloxy]-8-(3-methyl-2-octyl)-2-(2-propynyl)-1,2,3,4-tetrahydro-5H-[1]benzopyrano [3,4-d]pyridine or a pharmaceutically acceptable acid addition salt thereof.

6. A pharmaceutical composition comprising a therapeutically effective amount of a compound of claim 1 and a pharmaceutically acceptable carrier.

7. A pharmaceutical composition comprising a therapeutically effective amount of a compound of claim 3 and a pharmaceutically acceptable carrier.

8. A pharmaceutical composition comprising a therapeutically effective amount of a compound of claim 4 and a pharmaceutically acceptable carrier.

9. A pharmaceutical composition comprising a therapeutically effective amount of a compound of claim 5 and a pharmaceutically acceptable carrier.

10. A method of relieving pain comprising administering to a patient in pain a therapeutically effective amount of a compound of claim 1.

11. A method of relieving pain comprising administering to a patient in pain a therapeutically effective amount of a compound of claim 3.

12. A method of relieving pain comprising administering to a patient in pain a therapeutically effective amount of a compound of claim 4.

13. A method of relieving pain comprising administering to a patient in pain a therapeutically effective amount of a compound of claim 5.

* * * * *

UNITED STATES PATENT AND TRADEMARK OFFICE
CERTIFICATE OF CORRECTION

PATENT NO. : 4,042,694
DATED : August 16, 1977
INVENTOR(S) : Louis Selig Harris et al.

It is certified that error appears in the above-identified patent and that said Letters Patent are hereby corrected as shown below:

Column 2, last line, change "s" to --as--; column 4, line 32, change "3,755,586" to --3,755,584--; line 42, change "tivehynotic" to --tive-hypnotic--; line 49, change "sedativehypnotic" to --sedative-hypnotic--; line 54, change "sedativehynotic" to --sedative-hypnotic--; line 65, change "301mg" to --30 mg--; column 5, line 2, change "agne" to --agent--; line 7, change "has" to --had--; line 20, change "shown" to --show--; Col. 6, line 65, "indert" should be -- inert --. column 8, line 65, change "at" to --as--; column 10, line 8, change "H2O" to --H$_2$O--; column 12, line 34, change "dihkydrochloride" to --dihydrochloride--; column 13, line 18, change "yl10" to --yl-10--; line 19, change "pryidine" to --pyridine--; line 27, change "zopyrano 5H" to --zopyrano--; line 67, change "form" to --produce--; column 14, line 8, change "yl, 2, 3, 4" to --y-1, 2, 3, 4--; line 38, change "-2-2-" to -- -2- --; column 16, line 19, change "was" to --and--; column 18, line 26, change "-2-propynyl)" to -- -2-(2-propynyl)--.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks